US007345036B2

(12) United States Patent
Grove et al.

(10) Patent No.: US 7,345,036 B2
(45) Date of Patent: Mar. 18, 2008

(54) (PYRIDO/THIENO)—[F]—OXAZEPINE-5-ONE DERIVATIVES

(75) Inventors: Simon James Anthony Grove, Scotland (GB); Julia Adam-Worall, Scotland (GB); Minggiang Zhang, Kirkland (CA); Robert Gilfillan, Scotland (GB)

(73) Assignee: N.V. Organon, Oss (NL)

( * ) Notice: Subject to any disclaimer, the term of this patent is extended or adjusted under 35 U.S.C. 154(b) by 133 days.

(21) Appl. No.: 10/480,569

(22) PCT Filed: Jun. 10, 2002

(86) PCT No.: PCT/EP02/06364

§ 371 (c)(1),
(2), (4) Date: Jun. 14, 2004

(87) PCT Pub. No.: WO02/102808

PCT Pub. Date: Dec. 27, 2002

(65) Prior Publication Data

US 2004/0220175 A1    Nov. 4, 2004

(30) Foreign Application Priority Data

Jun. 14, 2001    (EP)    .................. 01202284

(51) Int. Cl.
*A61P 25/28*    (2006.01)
(52) U.S. Cl. .................................. 514/211.04
(58) Field of Classification Search ............ 514/211.04
See application file for complete search history.

(56) References Cited

U.S. PATENT DOCUMENTS 6,174,881 B1    1/2001    Borer et al.

FOREIGN PATENT DOCUMENTS

| DE | 19 54 839 A | 5/1970 |
|---|---|---|
| EP | 0 884 310 A | 12/1998 |
| GB | 1238719 | 7/1971 |
| WO | WO 94/02475 | 2/1994 |
| WO | 96 20941 A | 7/1996 |
| WO | 96 38414 A | 12/1996 |
| WO | 97 36907 A | 10/1997 |
| WO | 99 42456 A | 8/1999 |
| WO | WO 99/51240 | 10/1999 |

OTHER PUBLICATIONS

Sleevi M C et al: "Optical isomers of Rocastine and Close Analogues: Synthesis and H1 Antihistaminic Activity of its Enantiomers and their Structural Relationship to the Classical Antihistamines"; Journal of Medicinal Chemistry, American Chemical Society. Washington, US, vol. 34, No. 4, Apr. 1, 1991, pp. 1314-1328.

Bigge, C.F. et al.: "AMPA receptor agaonists, antagonists and modulators: their potential for clinical utility"; Exp. Opin. Ther. Patents, vol. 7, No. 10, Oct. 1997, pp. 1099-1114.

Alterman et al., "Fast Microwave-Assisted Preparation of Aryl and Vinyl Nitriles and the Corresponding Tetrazoles from Organohalides," *J. Org. Chem.* 65 (2000) 7984-7989.

Andrews et. al., "Effects of imipramine and mirtazapine on operant performance in rats," *Drug Dev. Res.* 32 (1994) 58-66.

Barn et.al., "Synthesis of Novel Analogues of the Delta Opioid Ligand SNC-80 Using $AlCl_3$-Promoted Aminolysis," *Biorg. Med. Chem. Lett.* 9 (1999)1329-34.

Brown et. al., "Selective Reductions. 30. Effect of Cation and Solvent on the Reactivity of Saline Borohydrides for Reduction of Carboxylic Esters. Improved Procedures for the Conversion of Esters to Alcohols by Metal Borohydrides," *J. Org. Chem.* 47 (1982) 4702-4708.

Grove et.al., "Positive Modulators of the AMPA Receptor," *Exp. Opin. Ther. Patents* 10 (2000) 1539-1548.

Hamill et. al., "Improved Patch-Clamp Techniques for High-Resolution Current Recording from Cells and Cell-Free Membrane Patches," *Pflügers Arch.* 391 (1981) 85-100.

Ireland et al., "Application of the Swern Oxidation to the Manipulation of Highly Reactive Carbonyl Compounds," *J. Org. Chem.* 50 (1985) 2198-2200.

Ito et. al., "Allosteric Potentiation of Quisqualate Receptors by a Nootropic Drug Aniracetarn," *J. Physiol.* 424 (1990) 533-543.

Krapcho, A.P., et. al. "Synthesis of Regioisomeric 6,9-(chlorofluoro)-Substituted Benzo[g]quinoline-5,10-diones, Benzo[g]isoquinoline-5,10-diones and 6-Chloro-9-fluorobenzo[g]quinozaline-5,10-dione," *J. Het. Chem.* 34 (1997) 27-31.

Lees, G.J., "Pharmacology of AMPA/Kainate Receptor Ligands and Their Therapeutic Potential in Neurological and Psychiatric Disorders," *Drugs* 59 (2000) 33-78.

Mitsunobu, O., "The Use of Diethyl Azodicarboxylate and Triphenylphosphine in Synthesis and Transformation of Natural Products," *Synthesis* 1 (1981), 1-28.

Pasquier et al., "Free and $Cr(CO)_3$-Complexed Aminophosphine Phosphinite Ligands for Highly Enantioselective Hydrogenation of α-functionalized Ketones," *Organometallics* 19 (2000) 5723-5732.

Reed et. al., "Structure—Activity Relationships of Cytotoxic Cholesterol-Modified DNA Duplexes," *J. Med Chem.* 38 (1995) 4587-4596.

Schoenberg A. et al. "Palladium-Catalyzed Carboalkoxylation of Aryl, Benzyl, and Vinylic Halides," *J. Org. Chem.* 39 (1974) 3318-3326.

(Continued)

*Primary Examiner*—Bruck Kifle
(74) *Attorney, Agent, or Firm*—Susan Hess

(57) ABSTRACT

The present invention relates to (pyrido/thieno)-[f]-oxazepine-5-one derivatives having the general Formula (I) or a pharmaceutically acceptable salt thereof. The invention also relates to pharmaceutical compositions comprising said derivatives, and to the use of these (pyrido/thieno)-[f]-oxazepine-5-one derivatives in the treatment of neurological diseases and psychiatric disorders which are responsive to enhancement of synaptic responses mediated by AMPA receptors in the central nervous system.

4 Claims, No Drawings

OTHER PUBLICATIONS

Schoenberg et al., "Palladium-Catalyzed Amidation of Aryl, Heterocyclic, and Vinylic Halides," *J. Org. Chem.* 39 (1974) 3327-3331.

Schultz et. al., "Regio- and Stereoselective Control in the Addition of Grignard Reagents to the Pyridine Ring System," *J. Org. Chem.* 51 (1986) 838-841.

Thurston et.al., "Synthesis and Reactivity of a Novel Oxazolo[2,3-*c*][1,4]benzodiazepine Ring System with DNA Recognition Potential: a New Class of Anthramycins," J. Chem. Soc., Chem. Commun. (1990) 874-876.

Wolfe J.P. et. al. "Simple, Efficient Catalyst System for the Palladium-Catalyzed Amination of Aryl Chlorides, Bromides, and Triflates," *J. Org. Chem.* 65 (2000) 1158-1174.

Yamada, K.A., "Therapeutic Potential of Positive AMPA Receptor Modulators in the Treatment of Neurological Disease," *Exp. Opin. Invest. Drugs* 9 (2000) 765-778.

Yamada et al., "Diazoxide Blocks Glutamate Desensitization and Prolongs Excitatory Postsynaptic Currents in Rat Hippocampal Neurons," *J. Physiol* 458 (1992) 409-423.

Peru Patent Office Technical Report PCG 66-1005/A, Nov. 4, 2006.

Olesen, Preben H., "The Use of Bioisosteric Groups in Lead Optimization," *Curr. Opin. Drug Discovery Dev.* 4(2001) 471-478.

(PYRIDO/THIENO)—[F]—OXAZEPINE-5-ONE DERIVATIVES

The present invention relates to (pyrido/thieno)-[f]-oxazepin-5-one derivatives, to pharmaceutical compositions comprising the same and to the use of these (pyrido/thieno)-[f]-oxazepin-5-one derivatives in the treatment of neurological and psychiatric diseases.

In the mammalian central nervous system (CNS), the transmission of nerve pulses is controlled by the interaction between a neurotransmitter, that is released by a sending neuron, and a surface receptor on a receiving neuron, which causes excitation of this receiving neuron. L-Glutamate is the most abundant neuro-transmitter in the CNS. It mediates the major excitatory pathway in mammals and is referred to as an excitatory amino acid (EAA). The excitatory amino acids are of great physiological importance, playing a role in a variety of physiological processes, such as learning and memory, the development of synaptic plasticity, motor control, respiration, cardiovascular regulation and sensory perception.

The receptors that respond to glutamate are called excitatory amino acid receptors (EAA receptors). These receptors are classified into two general types:
(1) "ionotropic" receptors that are directly coupled to the opening of cation channels in the cell membrane of the neurons, and (2) G-protein linked "metabotropic" receptors which are coupled to multiple secondary messenger systems that lead to enhanced phosphoinositide hydrolysis, activation of phospholipase D, increases or decreases in c-AMP formation and changes in ion channel function.

The ionotropic receptors can be pharmacologically subdivided into three subtypes, which are defined by the depolarizing actions of the selective agonists N-methyl-D-aspartate (NMDA), α-amino-3-hydroxy-5-methylisoxazole-4-propionic acid (AMPA), and kainic acid (KA).

Activation of synaptic AMPA receptors mediates a voltage independent fast (~1 ms to peak response) excitatory postsynaptic current (the fast EPSC), whereas activation of synaptic NMDA receptors generates a voltage-dependent, slow (~20 ms to peak response) excitatory current. The regional distribution of AMPA receptors in the brain suggests that AMPA receptors mediate synaptic transmission in those areas likely responsible for cognition and memory.

Activation of AMPA receptors by agonists is thought to lead to a conformational change in the receptor causing rapid opening and closing of the ion channel. The extent and duration of channel activation can either be decreased by a drug, which thereby acts as a negative allosteric modulator (e.g. GYKI 52466), or it can be enhanced by a drug, which is then acting as a positive allosteric modulator.

A structural class of AMPA receptor positive modulators derived from aniracetam (e.g. CX 516) are called Ampakines™. Positive modulators of the AMPA receptor can thus bind to the glutamate receptor and, upon subsequent binding of a receptor agonist, allow an ion flux through the receptor of increased duration.

Defects in glutamatergic neurotransmission may be associated with many human neurological and psychiatric diseases. The therapeutic potential of positive AMPA receptor modulators in the treatment of neurological and psychiatric diseases has been reviewed by Yamada, K. A. (*Exp. Opin. Invest. Drugs,* 2000, 9, 765-777), by Lees, G. J. (*Drugs,* 2000, 59, 33-78) and by Grove S. J. A. et al. (*Exp. Opin. Ther. Patents,* 2000, 10, 1539-1548).

Various classes of compounds that increase AMPA receptor function have been recognized and were recently reviewed by Grove S. J. A. et al. (supra). N-anisoyl-2-pyrrolidinone (aniracetam; Roche) is regarded as an Ampakine™ prototype (Ito, I. et al., *J. Physiol.* 1990, 424, 533-543), shortly thereafter followed by the discovery of certain sulphonamides (exemplified by cyclothiazide; Eli Lilly & Co) as AMPA modulators (Yamada, K. A. and Rothman, S. M., *J. Physiol.,* 1992, 458, 385-407). On the basis of the structure of aniracetam, derivatives thereof having improved potency and stability were developed by Lynch, G. S. and Rogers, G. A. as disclosed in International Patent Application WO 94/02475 (The Regents of the University of California). Additional ampakines in the form of benzoylpiperidines and pyrrolidines were subsequently disclosed in WO 96/38414 (Rogers, G. A. and Nilsson, L.; Cortex Pharmaceuticals), followed by compounds wherein the amide function was conformationally restricted in a benzoxazine ring system, as disclosed in WO 97/36907 (Rogers G. A. and Lynch. G., The Regents of the University of California; Cortex Pharmaceuticals), or in an acylbenzoxazine ring system, as disclosed in WO 99/51240 (Rogers G. A. and Johnström, P., The Regents of the University of California). Structurally related benzoxazine derivatives and especially 1,2,4-benzothiadiazine-1,2-dioxides, structurally derivatives of cyclothiazide™, have been disclosed in WO 99/42456 (Neurosearch A/S) as positive modulators of the AMPA receptor.

Positive AMPA receptor modulators have many potential applications in humans. For example, increasing the strength of excitatory synapses could compensate for losses of synapses or receptors associated with ageing and brain disease (Alzheimer's disease, for example). Enhancing AMPA receptor-mediated activity could cause more rapid processing by multisynaptic circuitries found in higher brain regions and thus could produce an increase in perceptual motor and intellectual performance. Ampakines have further been suggested to be potentially useful as memory enhancers, to improve the performance of subjects with sensory-motor problems and of subjects impaired in cognitive tasks, dependent upon brain networks utilizing AMPA receptors, in treating depression, alcoholism and schizophrenia, and in improving the recovery of subjects suffering from trauma.

It has been observed on the other hand that sustained AMPA receptor activation in experimental animals (for example, at high doses of some AMPA modulators, especially those that are potent inhibitors of receptor desensitization), can cause seizures and potentially also other proconvulsant side effects (Yamada, K. A., *Exp. Opin. Invest. Drugs,* 2000, 9, 765-777). In view of the potential of excitotoxicity on AMPA receptor activation (particularly by modulators of the thiadiazide class), there remains a need for the development of positive modulators having a sufficient therapeutic index.

To this end the present invention provides (pyrido/thieno)-[f]-oxazepin-5-one derivatives having the general formula I

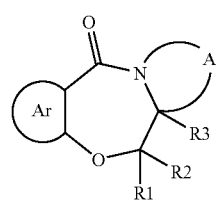

Formula I wherein

R$^1$, R$^2$ and R$^3$ are independently H or (C$_{1-4}$)alkyl;

Ar represents a fused thiophene or pyridine ring optionally substituted with one or more substituents selected from (C$_{1-4}$)alkyl, (C$_{1-4}$)alkyloxy, (C$_{1-4}$)alkyloxy(C$_{1-4}$)alkyl, CF$_3$, halogen, nitro, cyano, NR$^4$R$^5$, NR$^4$COR$^6$, and CONR$^4$R$^5$;

R$^4$ and R$^5$ are independently H or (C$_{1-4}$)alkyl; or R$^4$ and R$^5$ form together with the nitrogen atom to which they are bound a 5- or 6-membered saturated heterocyclic ring, optionally containing a further heteroatom selected from O, S or NR$^6$;

R$^6$ is (C$_{1-4}$)alkyl;

A represents the residue of a 4-7 membered saturated heterocyclic ring, optionally containing an oxygen atom, the ring being optionally substituted with 1-3 substituents selected from (C$_{1-4}$)alkyl, (C$_{1-4}$)alkyloxy, hydroxy, halogen and oxo; or a pharmaceutically acceptable salt thereof;

with the proviso that the compound of formula I wherein Ar represents a [3,2-f] fused pyridine ring; each of R$^1$-R$^3$ is H; and A represents (CH$_2$)$_3$; is excluded.

The pyrido-[3,2-f]-oxazepin-5-one derivative for which no protection per se is sought relates to a disclosure by Schultz, A. G. et al (J. Org. Chem. 1986, 51, 838-841) and Sleevi, M. C. et al (J. Med. Chem. 1991, 34, 1314-1328) wherein this pyrido-[3,2-f]-oxazepine-5-one derivative is described as a synthetic intermediate, without any pharmacological activity.

The (pyrido/thieno)-[f]-oxazepin-5-ones of formula I, including the prior art pyrido-[3,2-f]-oxazepin-5-one derivative described by Schultz et al. (supra), have been found to be positive AMPA receptor modulators, which can be useful in the treatment of neurological and psychiatric diseases where an enhancement of synaptic responses mediated by AMPA receptors is required.

In the definition of formula I Ar represents a fused pyridine or thiophene ring at the [f]-position of the oxazepine ring. The pyridine ring fusion can occur across the four possible bonds providing a pyrido[3,2-f]-, pyrido [4,3-f]-, pyrido[3,4-f]- or pyrido[2,3-f]-fused ring, respectively. The thiophene ring fusion can occur across three possible bonds providing a thieno[2,3-f]-, thieno[3,4-f]- or thieno[3,2-]-fused ring, respectively. The term (C$_{1-4}$)alkyl as used in the definition of formula I means a branched or unbranched alkyl group having 1-4 carbon atoms, like butyl, isobutyl, tertiary butyl, propyl, isopropyl, ethyl and methyl.

In the term (C$_{1-4}$)alkyloxy, (C$_{1-4}$)alkyl has the meaning as defined above.

The term (C$_{1-4}$)alkyloxy(C$_{1-4}$)alkyl means a (C$_{1-4}$)alkyl group which is substituted with (C$_{1-4}$)alkyloxy, both having the meaning as defined above.

The term halogen means F, Cl, Br or I.

In the definition of formula I R$^4$ and R$^5$ may form together with the nitrogen atom to which they are bound a 5- or 6-membered saturated heterocyclic ring, optionally containing a further heteroatom selected from O, S or NR$^6$. Examples of such heterocyclic ring substituents are piperidino, pyrrolidino, morpholino, N-methyl-piperazino, N-ethyl-piperazino and the like.

In the definition of formula I A represents the residue of a 4-7 membered saturated heterocyclic ring, optionally containing an oxygen atom, meaning that A is a bivalent radical containing 2-5 carbon atoms, such as ethylene, 1,3-propylene, 1,4-butylene, 1,5-pentylene, one carbon atom of which may be substituted by oxygen. Examples of 4-7 membered heterocyclic rings formed by residue A together with the nitrogen and carbon atom to which A is bonded are azetidine, pyrrolidine, piperidine, oxazolidine, isoxazolidine, morpholine, and azacycloheptane.

Preferred are the (pyrido/thieno)-[f]-oxazepin-5-one derivatives of formula I wherein R$^1$, R$^2$ and R$^3$ are H.

More preferred are compounds of formula I where Ar represents a [3,2-f] fused pyridine or a [2,3-f] fused thiophene ring.

The (pyrido/thieno)-[f]-oxazepin-5-one derivatives of the invention may be prepared by methods known in the art of organic chemistry in general. More specifically such compounds can be prepared using procedures outlined by A. G. Schultz et al (J. Org. Chem 1986, 51, 838-841) or by modification of those routes.

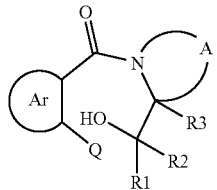

Formula II (Pyrido/thieno)-[f]-oxazepin-5-one derivatives of Formula I can for instance be prepared by cyclization of a compound according to formula II, wherein Ar, A and R$^1$-R$^3$ have the meaning as previously defined, any functional group with an acidic hydrogen being protected with a suitable protecting group, and wherein Q represents hydroxy, halogen or (C$_{1-4}$)alkyloxy, after which any protecting group, when present, is removed. The cyclization reaction for compounds wherein Q is halogen or (C$_{1-4}$) alkyloxy can be carried out in the presence of a base such as sodium hydride or cesium carbonate in a solvent such as dimethylformamide and at a temperature of 0-200° C., preferably 25-150° C.

For compounds of formula II wherein Q is a hydroxy group, cyclization can be effected under Mitsunobu conditions (Mitsunobu, O.,Synthesis 1981, 1) using a triarylphosphine for example triphenyl phosphine and a dialkyl azodicarboxylate, such as diisopropyl azodicarboxylate, in a solvent such as tetrahydrofuran.

Suitable protecting groups for functional groups which are to be temporarily protected during syntheses, are known in the art, for example from Wuts, P. G. M. and Greene, T. W.: Protective Groups in Organic Synthesis, Third Edition, Wiley, New York, 1999.

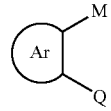

Formula III

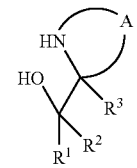

Formula IV

Compounds of formula II can be prepared from the condensation of a compound of formula III wherein Ar and Q have the meaning as previously defined and M represents a carboxylic acid or an derivative thereof, such as a carboxylic ester or a carboxylic acid halide, preferably a chloride or a bromide with a compound of formula IV where $R^1$-$R^3$ and A have the meaning as previously defined.

When M represents a carboxylic acid the condensation reaction, i.e. an acylation, can be effected with the aid of a coupling reagent, such as for example carbonyl diimidazole, dicyclohexylcarbodiimide and the like, in a solvent such as dimethylformamide or dichloromethane.

When M represents a carboxylic acid halide the condensation with the amine derivative IV can be carried out in the presence of a base, for example triethylamine, in a solvent such as methylene chloride.

When M represents a carboxylic acid ester derivative a direct condensation with the amine derivative of Formula IV can be carried out at an elevated temperature, for example at about 50 to 200° C. This condensation can also be performed using a Lewis acid, for example aluminum trichloride as described by D. R. Bam et al (*Biorg. Med. Chem. Lett.*, 1999, 9, 1329-34).

The preparation of compounds of formula I can be performed using the methods described above by employing a one pot two step procedure, meaning that a compound of formula II, which results from a condensation reaction between a compound of formula III with a compound of formula IV, is not isolated from the reaction mixture but further treated with a base to give compounds of formula I.

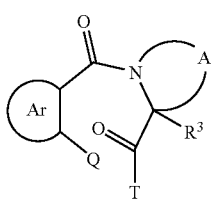

Formula V

Compounds of formula II may also be prepared from the reaction of a compound of formula V where Ar, $R^3$ and A are as defined above and T represents hydrogen, $C_{(1-4)}$alkyl, or $C_{(1-4)}$alkyloxy, with a $C_{(1-4)}$alkylmetal reagent, for example a Grignard reagent, in a solvent such as tetrahydrofuran.

A compound of formula II where $R^1$ represents a hydrogen and $R^2$ represents a $C_{(1-4)}$alkyl group may be prepared from a compound of formula V where T represents a $C_{(1-4)}$alkyl group by a reduction, for example sodium borohydride, in a solvent such as ethanol.

A compound of formula V where T represents an alkyloxy group may be prepared from a compound of formula III where M represents a carboxylic acid chloride and an alkanolamine imine derived from an alkyl glycolate as described by D. E. Thurston et al (*J. Chem. Soc., Chem. Commun.*, 1990, 874-876).

A compound of formula V may be prepared by coupling a compound of formula III, wherein Ar, M and Q have the meaning as previously defined, with a compound of formula VI, wherein $R^3$, A and T have the meaning as previously defined employing the methods described above for the coupling of compounds of formula III and IV.

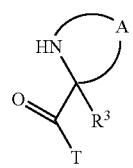

Formula VI

Compounds of formula III, IV and VI can be obtained from commercial sources, prepared by literature procedures or modifications of literature procedures known to those skilled in the art.

The skilled person will likewise appreciate that various compounds of Formula I can be obtained by appropriate conversion reactions of functional groups corresponding to certain of the substituents on the aromatic ring. For example, the reaction of a $(C_{1-4})$alkyl alcohol with a compound of formula I, wherein Ar, A and $R^1$-$R^3$ are as defined above, and wherein one or more of the substituents on the Ar ring is a leaving group such as, but not limited to, fluoro or chloro in the presence of a base such as sodium hydride gives compounds of formula I where one or more of the substituents on the Ar ring is $(C_{1-4})$alkyloxy.

Compounds of formula I where one or more of the substituents on the Ar ring are $CONR^4R^5$ may be prepared by conversion of a compound of formula I where one or more of the substituents on the aromatic ring are halo into the corresponding carboxylic acid ester using a palladium (II), for example dichlorobis(triphenylphosphine)palladium, catalysed carbonylation reaction as descibed by A. Schoenberg et al (*J. Org. Chem.* 1974, 39, 3318). The saponification of the ester to the carboxylic acid, using for example sodium hydroxide in tetrahydrofuran-water, and coupling of the carboxylic acid with an amine of formula $NHR^4R^5$ using, for example carbonyl diimidazole as coupling agent, gives compounds of formula I where one or more of the substituents on the aromatic ring is $CONR^4R^5$. The carboxylic acid precursor to compounds of formula I where one or more of the substituents on the aromatic ring are $CONR^4R^5$ may be prepared by the oxidation of a compound of formula I where one or more of the substituents on the aromatic ring is a methyl group using an oxidant, for example chromium trioxide. Compounds of formula I where one or more of of the substituents on the aromatic ring are $CONR^4R^5$ may be prepared by a palladium (II), such as dichlorobis(triphenylphosphine)palladium, catalysed carbonylation of a compound of formula I where one or more of the substituents on the aromatic ring are halo in the presence of an amine of formula $NHR^4R^5$ using the method descibed by A. Schoenberg and R. F. Heck (*J. Org. Chem.* 1974, 39, 3327).

A compound of formula I where one or more of the substituents on the Ar ring are CN may be prepared from a compound of formula I where one or more of the substituents on the Ar ring is $CONH_2$ by dehydration with a dehydrating agent, for example phosphorus oxychloride. A compound of formula I where one or more of the substituents on the Ar ring are CN may be prepared from a compound of formula I where one or more of the substituents on the Ar ring is bromo or iodo using a palladium (0) catalysed cyanation reaction as descibed by M. Alterman and A. Hallberg (*J. Org. Chem.* 2000, 65, 7984).

A compound of formula I where one or more of the substituents on the Ar ring are $NR^4R^5$ may be prepared from a compound of formula I where one or more of the substituents on the Ar ring is fluoro or chloro by displacement of the halogen with an amine of formula $NHR^4R^5$. A compound of formula I where one or more of the substituents on the Ar ring are $NR^4R^5$ may be prepared from a compound of formula I where one or more of the substituents on the Ar ring is chloro, bromo or iodo by a palladium catalysted amination reaction with an amine of formula $NHR^4R^5$ as described by J. P. Wolfe et al (*J. Org. Chem.* 2000, 65, 1158). A compound of formula I where one or more of the substituents on the Ar ring are $NR^4R^5$ and one of $R^4$ or $R^5$ is hydrogen may be prepared from a compound of formula I where one or more of the substituents on the Ar ring are $NR^4R^5$ and both $R^4$ and $R^5$ are H by alkylation of the nitrogen atom with an alkylating agent of formula $C_{(1-4)}$alkylY where Y is a leaving group such as an alkyl or aryl sulfonate, chloro, bromo or iodo. A compound of formula I where one or more of the substituents on the Ar ring are $NR^4R^5$ and both $R^4$ and $R^5$ are H may be prepared from a compound of formula I where one or more of the substituents on the Ar ring are nitro by a reduction for example a palladium catalysed reduction with hydrogen. A compound of formula I where one or more of the substituents on the Ar ring are $NR^4COR^6$ may be prepared from a compound of formula I where one or more of the substituents on the aromatic ring are $NHR^4$ by treatment with an acylating agent such as a $C_{(1-5)}$acid chloride or anhydride, for example acetic anhydride, in a solvent, for example pyridine.

Treatment of a compound of formula I, where A represents a residue of a 4-7 membered saturated heterocyclic ring substituted with 1-3 hydroxy groups, with a base, such as sodium hydride, in a solvent, such as tetrahydrofuran, with an alkylating agent of formula $C_{(1-4)}$alkylY where Y is defined as above gives a compound of formula I where A represents a residue of a 4-7 membered saturated heterocyclic ring optionally substituted with 1-3 alkyloxy groups.

In a compound of formula I, where A represents a residue of a 4-7 membered saturated heterocyclic ring substituted with 1-3 hydroxy groups, the hydroxy group(s) can be substituted by halogen by treatment with a halogenating reagent such as (diethylamino)sulfur trifluoride (DAST) or with the carbon tetrahalide-triphenylphosphine combination.

Similarly, a compound of formula I where A represents a residue of a 4-7 membered saturated heterocyclic ring optionally substituted with 2 halogen groups at the same carbon atom may be prepared from the corresponding oxo-derivative by treatment with a halogenating agent, such as DAST.

The oxidation of a compound of formula I, where A represents a residue of a 4-7 membered saturated heterocyclic ring optionally substituted with 1-3 hydroxy groups, with an oxidising agent, such as in the Swern oxidation as described by R. E. Ireland and D. W. Norbeck (*J. Org. Chem.* 1985, 50, 2198-2200), gives compounds of formula I where A represents a residue of a 4-7 membered saturated heterocyclic ring optionally substituted with 1-3 oxo groups.

The (pyrido/thieno)-[f]-oxazepin-5-one derivatives of Formula I and their salts contain at least one centre of chirality, and exist therefore as stereoisomers, including enantiomers, and when appropriate, diastereomers. The present invention includes the aforementioned stereoisomers within its scope and each of the individual R and S enantiomers of the compounds of formula I and their salts, substantially free, i.e. associated with less than 5%, preferably less than 2%, in particular less than 1% of the other enantiomer, and mixtures of such enantiomers in any proportions including the racemic mixtures containing substantially equal amounts of the two enantiomers. Methods for asymmetric synthesis whereby the pure stereoisomers are obtained are well known in the art, e.g. synthesis with chiral induction or starting from chiral intermediates, enantioselective enzymatic conversions, separation of stereoisomers or enantiomers using chromatography on chiral media. Such methods are for example described in *Chirality in Industry* (edited by A. N. Collins, G. N. Sheldrake and J. Crosby, 1992; John Wiley). Specific methods applicable for the stereoselective preparation of aryloxazepine derivatives of this invention are those described by Schultz, A. G. et al. (*J. Org. Chem.* 1986, 51, 838-841).

Pharmaceutically acceptable salts may be obtained by treating a free base of a compound according to formula I with a mineral acid such as hydrochloric acid, hydrobromic acid, phosphoric acid and sulphuric acid, or an organic acid such as for example ascorbic acid, citric acid, tartaric acid, lactic acid maleic acid, malonic acid, fumaric acid, glycolic acid, succinic acid, propionic acid, acetic acid, methane sulphonic acid, and the like.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a (pyrido/thieno)-[f]-oxazepin-5-one derivative having the general formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, intramuscular, local, or rectal administration, and the like, all in unit dosage forms for administration.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincoft Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The (pyrido/thieno)-[f]-oxazepin-5-one derivatives of the invention are AMPA receptor positive modulators, as can be determined by an increase in steady state current induced by application of glutamate in a conventional whole cell patch clamp method when a (pyrido/thieno)-[f]-oxazepin-5-one of the invention is present (see Example 10 and Table I). The compounds may be used in the treatment of neurological and psychiatric diseases where an enhancement of synaptic responses mediated by AMPA receptors is required, such as neurodegenerative disorders, cognitive or memory dysfunction, memory and learning disorders such as can result from ageing, attention disorder, trauma, stroke, epilepsy, Alzheimer's disease, depression, schizophrenia, psychotic disorders, sexual dysfunctions, autism, or a disorder or disease resulting from neurotic agents or substance abuse, and alcohol intoxication.

The compounds of the invention may be administered for humans in a dosage of 0.001-50 mg per kg body weight, preferably in a dosage of 0.1-20 mg per kg body weight.

The invention is illustrated by the following Examples:

EXAMPLE 1

(S)-2,3,10,10a-tetrahydro-1H,5H-pyrrolo[2,1-c]thieno[2,3-f][1,4]oxazepine-5-one

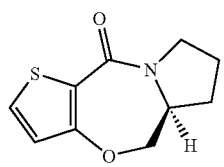

To a solution of 3-chlorothiophene-2-carboxylic acid (0.5 g; 6.325 mmol) in dimethylformamide (5 ml) was added 1,1'-carbonyldiimidazole (1.07 g; 6.64 mmol) and the solution stirred at room temperature for 1 h, followed by the addition of (S)-(+)-2-pyrrolidinemethanol (0.655 ml; 6.64 mmol). The reaction was stirred at room temperature overnight whereupon 60% sodium hydride in mineral oil (0.507 g; 12.7 mmol) was carefully added and the mixture was heated slowly to 150° C. with the progress of the reaction being monitored by thin layer chromatography. The reaction was cautiously diluted with water and extracted with ethyl acetate and the organic layer washed with water then dried (Na$_2$SO$_4$) and evaporated to give the crude product. Purification by flash chromatography eluting with 0-10% (v/v) methanol in dichloromethane followed by crystalisation from ethyl acetate-petroleum ether (40-60) afforded the title compound (0.15 g). M.p.: 167-167.5° C.; EIMS: m/z=222.2 [M+H]$^+$

EXAMPLE 2

The procedure described under Example 1 was further used to prepare the following compounds:

2A: (R)-2,3,10,10a-tetrahydro-1H,5H-pyrrolo[2,1-c]thieno[2,3-f][1,4]oxazepine-5 -one was obtained from 3-chlorothiophene-2-carboxylic acid and (R)-(−)-2-pyrrolidinemethanol. M.p.: 168-168.5° C.; EIMS: m/z=222.2 [M+H]$^+$ 2B: (S)-8-trifluoromethyl-2,3,11,11a-tetrahydro-1H,5H-pyrrolo[2,1-c]pyrido[3,2-f][1,4]-oxazepine-5-one was obtained from 2-chloro-6-trifluoromethylnicotinic acid and (S)-(+)-2 -pyrrolidinemethanol. M.p.: 152-153° C.; EIMS: m/z=273.2 [M+H]$^+$ 2C: (R)-8-trifluoromethyl-2,3,11,11a-tetrahydro-1H,5H-pyrrolo[2,1-c]pyrido[3,2-f][1,4]-oxazepine-5-one was obtained from 2-chloro-6-trifluoromethyinicotinic acid and (R)-(−)-2 -pyrrolidinemethanol. M.p.: 152-153° C.; EIMS: m/z=273.2 [M+H]$^+$

EXAMPLE 3

(S)-8-Methyl-2,3,11,11a-tetrahydro-1H,5H-pyrrolo[2,1-c]pyrido[3,2-f][1,4]oxazepine-5-one hydrochloride salt To a solution of 2-chloro-6-methylnicotinic acid (4.3 g; 25 mmol) in dimethylformamide (50 ml) was added 1,1'-carbonyldiimidazole (5 g; 30 mmol) and the solution stirred at room temperature for 1 h, followed by the addition of (S)-(+)-2-pyrrolidinemethanol (3.3 ml). The reaction was stirred at room temperature for 2 h then diluted with water and extracted with ethyl acetate. The organic layer was dried (Na$_2$SO$_4$) and evaporated to give the intermediate amide as an oil. This oil was taken up in dimethylformamide (50 ml) and cesium carbonate (7.8 g) added. The reaction was heated for 2 h at 60° C. then cooled to room temperature, partitioned between ethyl acetate and water. The organic layer was washed with water, dried (Na$_2$SO$_4$) and evaporated. Convertion to the hydrochloide salt with HCl in ether and crystallisation from methanol-ether afforded the title product. M.p.: 176-180° C.; EIMS: m/z=219.2 [M+H]$^+$

EXAMPLE 4

The procedure described under Example 3 was further used to prepare the following compounds:

4A: (S)-8-Chloro-2,3,11,11a-tetrahydro-1H,5H-pyrrolo[2,1-c]pyrido[3,2-f][1,4]oxa-zepine-5-one was obtained from 2,6-chloronicotinic acid and (S)-(+)-2 -pyrrolidinemethanol. M.p.: 164-166° C.; EIMS: m/z=239 [M+H]$^+$ 4B: (R)-8-Chloro-2,3,11,11a-tetrahydro-1H,5H-pyrrolo[2,1-c]pyrido[3,2-f][1,4]oxa-zepine-5-one was obtained from 2,6-dichloronicotinic acid and (R)-(−)-2-pyrrolidinemethanol. M.p.: 162-164° C.; EIMS: m/z=239.2 [M+H]$^+$ 4C: (S)-1,2,11,11a-Tetrahydroazetidinyl[2,1-c][1,4]pyrido[3,2-f][1,4]oxazepine-5-one was obtained from 2-chloronicotinic acid and (S)-(−)-2-hydroxymethylazetidine (C. Pasquier et al, Organometallics 2000, 19, 5723-5732). M.p.: 135-136° C.; EIMS: m/z=191.4 [M+H]$^+$ 4D: (±)-6,6a,7,8,9,10-hexahydro-12H-pyrido[2,1-c]pyrido[3,2-f][1,4]oxazepine-12-one was obtained from 2-chloronicotinic acid and 2-piperidinemethanol. M.p.: 86-87° C.; EIMS: m/z=239 [M+H]$^+$ 4E: (S)-2,3,11,11a-tetrahydro-1H,5H-pyrrolo[2,1-c]pyrido[4,3-f][1,4]oxazepine-5-one was obtained from 3-chloropyridine-4-carboxylic acid (A. P. Krapcho et al, *J. Het. Chem.* 1997, 34, 27-31) and (S)-(+)-2-pyrrolidinemethanol. M.p.: 153-155° C.; EIMS: m/z=205.2 [M+H]$^+$ 4F: (R)-2,3,11,11a-tetrahydro-1H,5H-pyrrolo[2,1-c]pyrido[4,3-f][1,4]oxazepine-5-one was obtained from 3-chloropyridine-4-carboxylic acid and (R)-(−)-2-pyrrolidinemethanol. M.p.: 156-157° C.; EIMS: m/z=205 [M+H]$^+$

EXAMPLE 5

(S)-7-Chloro-2,3,10,10a-tetrahydro-1H,5H-pyrrolo[2,1-c]thieno[3,2-f][1,4]oxazepine-5-one

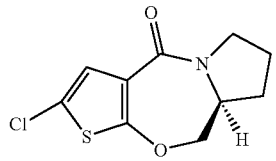

To methyl 2,5-dichlorothiophene-3-carboxylate (1.47 g; 7 mmol) was added (S)-(+)-2-pyrrolidinemethanol (1.75 g; 8.3 mmol). The reaction was stirred at 160° C. for 1 h then cooled to room temperature and dimethyl formamide (7.5 ml) and 60% sodium hydride in mineral oil (0.5 g; 12.5 mmol) was carefully added and the mixture was heated at 50° C. for 2 h. The reaction was quenched by the addition of isopropanol, evaporated and ethyl acetate added. The solution was washed with water and brine and evaporated. Crystallisation from ethyl acetate - petroleum ether afforded 307 mg of the title product M.p.: 162.5-163.5° C.; EIMS: m/z=244.2 [M+H]$^+$

EXAMPLE 6

The procedure described under Example 5 was further used to prepare the following compounds:

6A: (R)-7-Chloro-2,3,10,10a-tetrahydro-1H,5H-pyrrolo[2,1-c]thieno[3,2-f][1,4]oxa-zepine-5-one was obtained from (R)-(−)-2-pyrrolidinemethanol. M.p.: 162.5-163.5° C.; EIMS: m/z=244.2 [M+H]$^+$ 6B: (2R,10aS)-7-Chloro-2-Hydroxy-2,3,10,10a-tetrahydro-1H,5H-pyrrolo[2,1-c ]thieno[3,2-f][1,4]oxazepine-5-one was obtained from methyl 2,5-dichlorothiophene-3-carboxylate and (3R, 5S)-3-hydroxy-5-hydroxymethylpyrrolidine (M. W. Reed et al, *J. Med. Chem.*, 1995, 38, 4587-4596) using the cesium carbonate cyclisation conditions described in example 3. M.p.: 193.5-194° C.; EIMS: m/z=260 [M+H]$^+$

EXAMPLE 7

(S)-8-Methoxy-2,3,11,11a-tetrahydro-1H,5H-pyrrolo[2,1-c]pyrido[3,2-f][1,4]oxazepine-5-one To a solution of the material prepared in Example 4A (1.2 g) in methanol (20 ml) was added sodium methoxide (0.27 g). The solution was refluxed for 2 h then evaporated, taken up in dichloromethane and washed with water and dried over sodium sulfate. The organic layer was evaporated and the resulting solid recrystallised from dichloromethane-ether-petroleum ether to give the title product (200 mg). M.p.: 136-138° C.; EIMS: m/z=253.0 [M+H]$^+$

EXAMPLE 8

(S)-8-piperidinyl-2,3,11,11a-tetrahydro-1H,5H-pyrrolo[2,1-c]pyrido[3,2-f]]1,4]oxazepine-5-one To a solution of the material prepared in Example 4A (600 mg) in dimethylformamide (20 ml) was added piperidine (0.26 ml). The solution was heated for 2 h then cooled, diluted with water and extracted with ethyl acetate. The organic layer was washed with water, dried (Na$_2$SO$_4$) and evaporated and the resulting solid recrystallised from dichloromethane-petroleum ether to give the title product (650 mg). M.p.: 148-152° C.; EIMS: m/z=288.0.[M+H]$^+$

EXAMPLE 9

(2R,11aS)-2-hydroxy-2,3,11,11a-tetrahydro-1H,5H-pyrrolo[2,1-c]pyrido[3,2-f][1, 4]oxazepine-5-one To a solution of (3R, 5S)-3-hydroxy-5-hydroxymethylpyrrolidine HCl salt (874 mg; M. W. Reed et al, *J. Med. Chem.*, 1995, 38, 4587-4596) in water (20 ml) was added sodium hydrogen carbonate (960 mg; 5.7 mmol) followed by 2-chloronicotinyl chloride (1.0 g; 5.7 mmol). The mixture was stirred for 2 days then extracted with dichloromethane, evaporated and purified by flash chromatography eluting with 10% methanol in dichloromethane to give the intermediate amide which was cyclised using the conditions described for example 3 to give the title product.

M.p.: 174° C.; EIMS: m/z=221.4 [M+H]$^+$

EXAMPLE 10

Patch Clamp Whole Cell Electrophysiology

A: Cell Culture.

Hippocampal neuronal cultures were prepared from embryonic or 1-3 day old Sprague-Dawley rats which were decapitated and the heads immediately placed in ice cold HBS (HEPES Buffered Solution: 130 mM NaCl, 5.4 mM KCl, 10 mM HEPES, 1.0 mM MgCl$_2$, 1.8 CaCl$_2$, 25 mM glucose, adjusted to pH 7.4). The whole brain was excised and placed on pre-sterilised filter paper, soaked in HBS and the cerebellum was removed. The brain was chopped and an enzyme solution (0.5 mg/ml protease X and 0.5 mg/ml protease in HBS) was added and subsequently left for 40 minutes at room temperature to digest before trituration. Cells were resuspended and then counted to give a final concentration of 1.5×10$^6$ per ml. Cells were aliquoted onto poly-D-lysine- and Matrigel®-treated coverslips and left to incubate at 37° C. for 1-2 hours. When incubation was complete, 1 ml of growth medium was added to each well containing a coverslip and the cells were returned to the incubator. After 3-5 days the mitotic inhibitor cytosine arabinoside (5 μM) was added and the cells returned to the incubator until required.

B: Patch Clamp Recording.

The whole cell configuration of the patch clamp technique (Hamill et al., *Pflügers Arch.* 1981, 39, 85-100) was used to measure glutamate-evoked currents from postnatal hippocampal neurons maintained in culture for 4-7 days. A glass coverslip containing the culture was transferred to the recording chamber (Warner Instrument Corp., Hamden, Conn.) mounted on the stage of an inverted microscope (Nikon, Kingston, UK). The recording chamber contained 1-2 ml extracellular solution (145 mM NaCl, 5.4 mM KCl, 10 mM HEPES, 0.8 mM MgCl$_2$, 1.8 CaCl$_2$, 10 mM glucose and 30 mM sucrose, adjusted to pH 7.4 with 1 M NaOH) and was constantly perfused at a rate of 1 ml/min. Recordings were performed at room temperature (20-22° C.) using an Axopatch 200B amplifier (Axon Instruments Ltd., Foster City, Calif.). Data acquisition and analysis was performed using Signal software (Cambridge Electronic Design Ltd., Cambridge, UK). Pipettes were manufactured from GC120F-10 glass (Harvard Apparatus, Edenbridge UK) using a model P-87 electrode puller (Sutter Instruments Co., Novarto, Calif.). The patch electrodes had typical resistances of between 3-5 MΩ when filled with intracellular solution (140 mM potassium gluconate, 20 mM HEPES, 1.1 mM EGTA, 5 mM phosphocreatine, 3 mM ATP, 0.3 mM GTP, 0.1 mM CaCl$_2$, 5 mM MgCl$_2$, adjusted to pH 7.4 with 1M KOH). Cells were voltage clamped at a holding potential of −60 mV and glutamate (0.5 mM) was applied using a 12 channel semi-rapid drug application device (DAD-12. Digitimer Ltd., Welwyn Garden city, UK). The agonist glutamate was applied for 1 s every 30 s. The response did not "run-down" over time using the whole-cell configuration. Between applications saline flowed to clear any dead volume in the system. For each application steady-state currents were plotted from the difference in baseline and steady state current and averaged over 300 ms.

Two solutions of the compound in extracellular solution were made up, one with glutamate and one without. The protocol was: 10 second application of compound, 1 second application of compound+glutamate and then 10 second wash with saline, then a 10 second delay. When the compound was not soluble, 0.5% DMSO was used as a co-solvent. Results are presented in Table I as the percentage increase in steady state current at 10 μM concentration of the compound of the invention in extracellular solution.

TABLE I

| Compound | % Increase in steady state current at 10 μM |
| --- | --- |
| (S)-2,3,11,11a-tetrahydro-1H,5H-pyrrolo[2,1-c]pyrido[3,2-f][1,4]-oxazepine-5-one* | 22 |
| (S)-2,3,10,10a-tetrahydro-1H,5H-pyrrolo[2,1-c]thieno[2,3-f][1,4]-oxazepine-5-one (Example 1) | 32 |
| (R)-2,3,10,10a-tetrahydro-1H,5H-pyrrolo[2,1-c]thieno[2,3-f][1,4]-oxazepine-5-one (Example 2A) | 20 |
| (S)-8-trifluoromethyl-2,3,11,11a-tetrahydro-1H,5H-pyrrolo[2,1-c]-pyrido[3,2-f][1,4]oxazepine-5-one (Example 2B) | 21 |
| (R)-8-trifluoromethyl-2,3,11,11a-tetrahydro-1H,5H-pyrrolo[2,1-c]-pyrido[3,2-f][1,4]oxazepine-5-one (Example 2C) | 19 |
| (S)-8-Methyl-2,3,11,11a-tetrahydro-1H,5H-pyrrolo[2,1-c]pyrido[3,2-f][1,4]-oxazepine-5-one hydrochloride salt (Example 3) | 12 |
| (S)-8-Chloro-2,3,11,11a-tetrahydro-1H,5H-pyrrolo[2,1-c]pyrido[3,2-f][1,4]-oxazepine-5-one (Example 4A) | 16 |
| (R)-8-Chloro-2,3,11,11a-tetrahydro-1H,5H-pyrrolo[2,1-c]pyrido[3,2-f][1,4]-oxazepine-5-one (Example 4B) | 29 |
| (±)-6,6a-7,8,9,10-hexahydro-12H-pyrido[2,1-c]pyrido[3,2-f][1,4]-oxazepine-12-one (Example 4D) | 13 |
| (S)-7-Chloro-2,3,10,10a-tetrahydro-1H,5H-pyrrolo[2,1-c]thieno[3,2-f][1,4]-oxazepine-5-one (Example 5) | 16 |
| (R)-7-Chloro-2,3,10,10a-tetrahydro-1H,5H-pyrrolo[2,1-c]thieno[3,2-f][1,4]-oxazepine-5-one (Example 6A) | 20 |
| (S)-8-Methoxy-2,3,11,11a-tetrahydro-1H,5H-pyrrolo[2,1-c]pyrido[3,2-f]-[1,4]oxazepine-5-one (Example 7) | 22 |

*: prepared as described by Schultz, A.G. et al (J. Org. Chem. 1986, 51, 838-841) who use the alternative naming: 1,2,3,10,11,11a(S)-hexahydro-5H-pyrrolo[2,1-c]pyrido[3,2-f][1,4]oxazepine-5-one; Sleevi, M.C. et al (J. Med. Chem. 1991, 34, 1314-1328) have used the name 6a,7,8,9-tetrahydro-6H,11H-pyrido[3,2-f]pyrrolo[2,1-c][1,4]oxazepine-11-one for this compound.

EXAMPLE 11

Differential Reinforcement of Low Rates of Responding, 72 Seconds (DRL72)

Rats are pretrained in a standard operant chamber to perform a DRL72 procedure according to Andrews et al (Andrews J S, Jansen J H M, Linders S, Princen A, Drinkenburg W H I M, Coenders C J H and Vossen J H M (1994).

Effects of imipramine and mirtazapine on operant performance in rats. Drug Development Research, 32, 58-66). The test session lasts for 60 minutes with no limit to the number of trials. Each trial begins with the stimulus light on above the active lever. A response on the lever only results in delivery of a pellet if 72 seconds has elapsed. A response on the lever before 72 seconds has elapsed resets the timer and is not rewarded. The number of pellets earned and the number of lever presses is recorded and used to calculate an efficiency score. Test compounds are administered via the intraperitoneal route 30 minutes before the start of the test session. Antidepressants increase the number of pellets earned and decrease the number of lever presses. (S)-2,3,11,11a-tetrahydro-1H,5H-pyrrolo[2,1-c]pyrido[3,2-f][1,4]oxazepine-5-one exhibited an antidepressant like profile.

EXAMPLE 12

Inhibition of Amphetamine-Induced Hyperlocomotion

Mice were injected sc with drug treatment or vehicle control. 30 Minutes later mice were injected sc with 1.5 mg/kg d-amphetamine sulphate or saline and immediately placed in infra red locomotor boxes where locomotor activity (long duration beam breaks of two adjacent beams) and stereotypic behaviour (repetitive short-duration beam breaks) were measured for a period of 60 minutes. The experiment was analysed using a 3-Way ANOVA with experimental session, infra red locomotor boxes and treatment as factors, and in the case of treatment, significant effects were followed up using a Tukey (HSD) test. (S)-2,3,11,11a-tetrahydro-1H,5H-pyrrolo[2,1-c]pyrido[3,2-f]and (S)-2,3,10,10a-tetrahydro-1H,5H-pyrrolo[2,1-c]thieno[2,3-f][1,4]oxazepine-5-one (Example 1) inhibited amphetamine induced hyperlocomotion.

The invention claimed is:

1. A pharmaceutical composition, comprising: a compound of Formula I

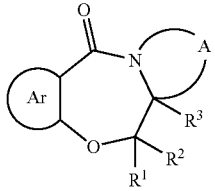

Formula I wherein $R^1$, $R^2$ and $R^3$ are independently H or $(C_{1-4})$alkyl;

Ar represents a fused thiophene or pyridine ring optionally substituted with one or more substituents selected from $(C_{1-4})$alkyl, $(C_{1-4})$alkyloxy, $(C_{1-4})$alkyloxy$(C_{1-4})$alkyl, $CF_3$, halogen, nitro, cyano, $NR^4R^5$, $NR^4COR^6$, and $CONR^4R^5$;

$R^4$ and $R^5$ are independently H or $(C_{1-4})$alkyl; or $R^4$ and $R^5$ form together with the nitrogen atom to which they are bound a 5- or 6-membered saturated heterocyclic ring, optionally containing a further heteroatom selected from O, S or $NR^6$;

$R^6$ is $(C_{1-4})$alkyl;

A represents a $C_{2-5}$ alkylene wherein a carbon atom may be replaced by an oxygen atom, the ring being optionally substituted with 1-3 substituents selected from $(C_{1-4})$alkyl, $(C_{1-4})$ alkyloxy, hydroxy, halogen and oxo; or a pharmaceutically acceptable salt thereof, and a pharmaceutically acceptable carrier.

2. A method of treating a neurological disease or a psychiatric disorder in a patient, which disease or disorder is responsive to enhancement of synaptic responses mediated by AMPA receptors in the central nervous system, and wherein the neurological disease or psychiatric disorder is selected from the group consisting of depression and schizophrenia, comprising:

administering of a therapeutically effective amount of a compound according to Formula I

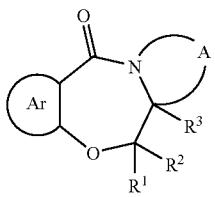

Formula I wherein $R^1$, $R^2$ and $R^3$ are independently H or ($C_{1-4}$alkyl;

Ar represents a fused thiophene or pyridine ring optionally substituted with one or more substituents selected from ($C_{1-4}$alkyl, ($C_{1-4}$)alkyloxy, ($C_{1-4}$alkyloxy($C_{1-4}$alkyl, $CF_3$, halogen, nitro, cyano, $NR^4R^5$, $NR^4COR^6$, and $CONR^4R^5$;

$R^4$ and $R^5$ are independently H or ($C_{1-4}$)alkyl; or $R^4$ and $R^5$ form together with the nitrogen atom to which they are bound a 5- or 6-membered saturated heterocyclic ring, optionally containing a further heteroatom selected from O, S or $NR^6$;

$R^6$ is ($C_{1-4}$)alkyl;

A represents a $C_{2-5}$ alkylene wherein a carbon atom may be replaced by an oxygen atom, the ring being optionally substituted with 1-3 substituents selected from ($C_{1-4}$alkyl, ($C_{1-4}$) alkyloxy, hydroxy, halogen and oxo; or a pharmaceutically acceptable salt thereof.

3. The method according to claim 2, wherein the neurological disease or psychiatric disorder is depression.

4. The method according to claim 2, wherein the neurological disease or psychiatric disorder is schizophrenia.

* * * * *